(12) United States Patent
Medo et al.

(10) Patent No.: US 8,821,878 B2
(45) Date of Patent: Sep. 2, 2014

(54) COMPOSITIONS OF HUMAN LIPIDS AND METHODS OF MAKING AND USING SAME

(71) Applicant: Prolacta Bioscience, Inc., City of Industry, CA (US)

(72) Inventors: Elena M. Medo, Murrieta, CA (US); Scott Eaker, Thousand Oaks, CA (US)

(73) Assignee: Prolacta Bioscience, Inc., City of Industry, CA (US)

( * ) Notice: Subject to any disclaimer, the term of this patent is extended or adjusted under 35 U.S.C. 154(b) by 0 days.

(21) Appl. No.: 13/740,788

(22) Filed: Jan. 14, 2013

(65) Prior Publication Data

US 2013/0195989 A1    Aug. 1, 2013

Related U.S. Application Data

(63) Continuation of application No. 12/518,237, filed as application No. PCT/US2007/086973 on Dec. 10, 2007, now Pat. No. 8,377,445.

(60) Provisional application No. 60/869,150, filed on Dec. 8, 2006.

(51) Int. Cl.
*A61K 39/00* (2006.01)
*A61K 35/20* (2006.01)
*A23L 3/10* (2006.01)

(52) U.S. Cl.
USPC ........ 424/157.1; 424/535; 424/522; 426/504; 426/409; 426/478; 426/491; 426/607; 514/775; 514/72; 514/547; 514/560

(58) Field of Classification Search
None
See application file for complete search history.

(56) References Cited

U.S. PATENT DOCUMENTS

| | | |
|---|---|---|
| 2,567,898 A | 9/1951 | Staaff |
| 3,946,113 A | 3/1976 | Seiberling |
| 4,362,697 A | 12/1982 | Tabb et al. |
| 4,455,483 A | 6/1984 | Schonhuber |
| 4,762,822 A | 8/1988 | Ettinger |
| 4,772,262 A | 9/1988 | Grant et al. |
| 4,876,100 A | 10/1989 | Holm et al. |
| 4,948,599 A | 8/1990 | Sagara et al. |
| 5,064,674 A | 11/1991 | Girsh |
| 5,169,766 A | 12/1992 | Schuster et al. |
| 5,256,437 A | 10/1993 | Degen et al. |
| 5,303,598 A | 4/1994 | Binder |
| 5,334,822 A | 8/1994 | Sanford |

(Continued)

FOREIGN PATENT DOCUMENTS

| | | | |
|---|---|---|---|
| EP | 1637043 | 3/2006 | |
| GB | 1451747 | * 10/1976 | ............... A10J 11/00 |

(Continued)

OTHER PUBLICATIONS

"International Search Report," 2 pages, PCT appl. No. PCT/US2012/049590 (mailed Oct. 1, 2012).

(Continued)

*Primary Examiner* — Yate K Cutliff
(74) *Attorney, Agent, or Firm* — Cooley LLP

(57) ABSTRACT

The disclosure features methods of making compositions that include a human lipid. The methods can include: obtaining whole human milk; separating the milk into a cream portion and a skim portion; processing the cream portion; and pasteurizing the processed cream portion.

9 Claims, 2 Drawing Sheets

(56) References Cited

U.S. PATENT DOCUMENTS

| | | | |
|---|---|---|---|
| 5,401,523 A | 3/1995 | Degen et al. | |
| 5,505,955 A * | 4/1996 | Peterson et al. | 424/439 |
| 5,541,065 A | 7/1996 | Erlich et al. | |
| 5,576,040 A | 11/1996 | Moller et al. | |
| 5,605,689 A | 2/1997 | Ammann | |
| 5,616,483 A | 4/1997 | Bjursell et al. | |
| 5,670,196 A | 9/1997 | Gregory | |
| 5,683,733 A | 11/1997 | Krabsen et al. | |
| 5,707,678 A | 1/1998 | Gregory | |
| 5,972,337 A | 10/1999 | Ceriani et al. | |
| 5,983,198 A | 11/1999 | Mowery | |
| 6,004,288 A | 12/1999 | Hochstedler et al. | |
| 6,017,511 A | 1/2000 | Wong et al. | |
| 6,020,015 A | 2/2000 | Gaull | |
| 6,056,978 A | 5/2000 | Beck et al. | |
| 6,183,803 B1 | 2/2001 | Morcol et al. | |
| 6,194,009 B1 | 2/2001 | Kamerel | |
| 6,270,827 B1 | 8/2001 | Gaull et al. | |
| 6,294,206 B1 | 9/2001 | Barrett-Reis et al. | |
| 6,613,367 B1 | 9/2003 | Wells et al. | |
| 6,635,296 B1 | 10/2003 | Nissen et al. | |
| 6,652,900 B2 | 11/2003 | Lindquist | |
| 6,670,124 B1 | 12/2003 | Chow et al. | |
| 6,737,096 B2 | 5/2004 | Lindquist | |
| 6,780,987 B1 | 8/2004 | Herman et al. | |
| 6,846,298 B1 | 1/2005 | Carr et al. | |
| 6,910,594 B2 | 6/2005 | Foley et al. | |
| 7,867,541 B2 | 1/2011 | McMahon et al. | |
| 7,914,822 B2 | 3/2011 | Medo | |
| 7,943,315 B2 | 5/2011 | Medo et al. | |
| 7,951,410 B2 | 5/2011 | McMahon et al. | |
| 8,278,046 B2 | 10/2012 | Medo et al. | |
| 2001/0034614 A1 | 10/2001 | Fletcher-Haynes et al. | |
| 2001/0049096 A1 | 12/2001 | Brown | |
| 2002/0155445 A1 | 10/2002 | Jarvik | |
| 2002/0182243 A1 | 12/2002 | Medo | |
| 2003/0093171 A1 | 5/2003 | Soehnlen | |
| 2003/0152942 A1 | 8/2003 | Fors et al. | |
| 2003/0175701 A1 | 9/2003 | Griffiths et al. | |
| 2003/0219812 A1 | 11/2003 | Quay et al. | |
| 2004/0181205 A1 | 9/2004 | Morton et al. | |
| 2004/0265462 A1 | 12/2004 | Carlson | |
| 2005/0053707 A1 | 3/2005 | Kopf et al. | |
| 2005/0096295 A1 | 5/2005 | McMahon et al. | |
| 2005/0100634 A1 | 5/2005 | Medo | |
| 2005/0214358 A1 | 9/2005 | Mikoshiba et al. | |
| 2005/0220894 A1 | 10/2005 | Williams et al. | |
| 2006/0115558 A1 | 6/2006 | Lamothe | |
| 2006/0204632 A1 | 9/2006 | Barrett-Reis et al. | |
| 2006/0233915 A1 | 10/2006 | Puski et al. | |
| 2007/0098863 A1 | 5/2007 | Medo et al. | |
| 2007/0104700 A1 | 5/2007 | Garcia-Rodenas et al. | |
| 2007/0203802 A1 | 8/2007 | Medo et al. | |
| 2008/0118615 A1 | 5/2008 | Hartmann et al. | |
| 2008/0124430 A1 | 5/2008 | Medo et al. | |
| 2008/0187619 A1 | 8/2008 | Hartmann et al. | |
| 2008/0227101 A1 | 9/2008 | Medo et al. | |
| 2008/0254165 A1 | 10/2008 | Patel et al. | |
| 2008/0274230 A1 | 11/2008 | Johns et al. | |
| 2009/0181848 A1 | 7/2009 | Lenz et al. | |
| 2009/0203592 A1 | 8/2009 | Beermann et al. | |
| 2009/0258121 A1 | 10/2009 | Medo | |
| 2010/0268658 A1 | 10/2010 | Medo et al. | |
| 2011/0206684 A1 | 8/2011 | Medo | |
| 2011/0311689 A1 | 12/2011 | Medo et al. | |

FOREIGN PATENT DOCUMENTS

| | | |
|---|---|---|
| GB | 1451747 A | 10/1976 |
| JP | 61-33895 U | 1/1986 |
| JP | 64-67141 A | 3/1989 |
| JP | 6-303900 A | 11/1994 |
| JP | 2002-532074 A | 10/2002 |
| JP | 2002-540806 A | 12/2002 |
| JP | 2005-525116 A | 8/2005 |
| SE | 380422 B | 11/1975 |
| WO | WO 98/57549 | 1/1998 |
| WO | WO-00/43550 | 7/2000 |
| WO | WO 2005/013709 A1 | 2/2005 |
| WO | WO 2005/051088 A2 | 6/2005 |
| WO | WO 2005/084129 | 9/2005 |
| WO | WO 2006/026878 A1 | 3/2006 |
| WO | WO 2006/026879 | 3/2006 |
| WO | WO/2007/035870 | 3/2007 |
| WO | WO-2008/027572 | 3/2008 |
| WO | WO-2008/067486 | 6/2008 |
| WO | WO 2008/073888 A2 | 6/2008 |
| WO | WO 2010/030764 A2 | 3/2010 |

OTHER PUBLICATIONS

"Written Opinion of the International Searching Authority," 6 pages, PCT appl. No. PCT/US2012/049590 (mailed Oct. 1, 2012).

Arnold, "How North American Donor Banks Operate: Results of a Survey: Part 2,"*J. Hum. Lact.*, 13(3):243-46, Sep. 1997.

Arnold, "How to Order Banked Donor Milk in the United States: What the Health Care Provider Needs to Know," J. Hum. Lact. 14(1):65-67 (1998).

Bernsahw, N.J., "Milk Banking: an Idea That Has Come of Age. Non-Profit Milk Banking," Seminar delivered at Utah Breastfeeding Coalition Meeting, Aug. 29, 2006.

Boehm, G., et al., "Metabolic Differences Between AGA- and SGA-Infants of Very Low Birthrate II Relationship to Protein Intake," Acta Paediatrics Scaninavica, Almquist, Och Wiksell, Stockholm, SE 77(5):642-646, Jan. 1, 1988.

Burger and Schumm, "Detection of a Minor contributor in a DNA Sample Mixture from Human Milk," *International Congress Series*, 1288:547-549, 2006.

Burger et al., "Detection of a 1% to 2% Contributor in a DNA Sample Mixture From Human Milk," International Society for Forensic Genetics 21$^{st}$ Congress Conference Programme and Abstracts [online], Sep. 12-17, 2005 [retrieved on Mar. 26, 2007]. Retrieved from the Internet: http://www.ipatimup.pt/isfg2005/PROGRAMME.pdf; p. 75.

Carey et al., "Growth and phosphorus metabolism in premature infants fed human milk, fortified human milk, or special premature formula. Use of serum procollagen as a marker of growth," Am. J. Dis. Children 141(5):511-515 (1987).

Casey, "The nutritive and metabolic advantages of homologous milk," Proc. Nutr. Soc. 48:271-281 (1989).

Cowan et al., "Milk permeate as a dietary supplement for lactating dairy cows," Aus. J. Exp. Agric. 30(6):807-810 (1990).

Davies, D. P., "Adequacy of Expressed Breast Milk for Early Growth of Preterm Infants," Arch. Disease in Childhood. 1977. vol. 52, pp. 296-301.

Friis and Andersen, "Rate of inactivation of cytomegalovirus in raw banked milk during storage at −20° C. and pasteurisation," Br. Med. J. 285:1604-1605 (1982).

Fukushima et al., "Consumption of cow milk and egg by lactating women and the presence of β-lactoglobulin and ovalbumin in breast milk," Am. J. Clin. Nutr. 65:30-35 (1997).

Gartner et al., "Breastfeeding and the use of human milk," Pediatr. 115(2):496-506 (2005).

Geilman et al., "Production of an electrolyte beverage from milk permeate," J. Dairy Sci. 75(9):2364-2369 (1992).

Hagelberg S., et al., "Amino Acid Levels in the Critically Ill Preterm Infant Given Mother's Milk Fortified with Protein from Human or Cow's Milk" Acta Paediatr Scan.1990. vol. 79, pp. 1163-1174.

Hagelberg, S., et al., "The Protein Tolerance of Very Low Birth Weight Infants Fed Human Milk Protein Enriched Mothers' Milk" Acta Paediatr Scan. 1982. vol. 71, pp. 597-601.

Hartmann, B.T., et al. "Best Practice Guidelines for the Operation of a Donor Human Milk Bank in an Australian NICU," *Early Human Devel.* 83:667-673, 2007.

Hylmo, P., et al., "Preparation of Fat and Protein from Banked Human Milk: Its Use in Feeding Very-Low-Birth-Weight Infants," Human Milk Banking, edited by A.F. Williams and J.D. Baum, Nestle Nutrition, Vewey/Raven Press, New York, 1984, pp. 55-61.

(56) References Cited

OTHER PUBLICATIONS

Itabashi et al., "Fortified preterm human milk for very low birth weight infants," Early Hum. Devel. 29:339-343 (1992).
Jenness and Palmer, "Substances Adsorved on the Fat Golbules in Cream and Their Relation to Churning. V. Composition of the 'Membrane' and Distribution of the Adsorbed Substances in Churning," J. Dairy Science 28(8):611-623, 1945.
Jensen et al., "Lipids of Bovine and Human Milks: A Comparison," J. Dairy Science 73:223-40, 1990.
Jensen, R.G. et al., "Lipids in Human and Infant Formulas," Annual Review of Nutrion, 12:417-441, Jul. 1, 1992.
Klein, Catherine, J., "Nutrient Requirements for Preterm Infant Formulas 123," Life Sciences Research Office, J Nutr 132:1935S-1577S, 2002.
Krukovsky et al., "The Effects of Nordihydroguaiaretic Acid, Salt, and Temperature of Storage on the Stability of Fat and Fat-Soluble Vitamins in Cream and Butter," J. Dairy Science, 32(7):679-87, 1949.
Lapillione, et al., "Mineral balance and whole body bone mineral content in very low-birth-weight infants", (1994) Acta Pediatrica 84 (s405):117-122.
Lawrence, "Storage of human milk and the influence of procedures on immunological components of human milk," Acta Pædiatr. 88:14-18 (1999).
Lindblad B.S., et al., "Blood Levels of Critical Amino Acids in Very Low Birthweight Infants on a High Human Milk Protein Intake" Acta Paediatr Scan.1982.vol. 296, pp. 24-27.
Lönnerdal, "Biochemistry and physiological function of human milk proteins," Am. J. Clin. Nutr. 42:1299-1317 (1985).
Lucas et al., "A human milk formula," Early Hum. Devel. 4/1:15-21 (1980).
Luck and Nau, "Nicotine and cotinine concentrations in the milk of smoking mothers: influence of cigarete consumption and diurnal variation," Eur J. Pediatr. 146:21-26 (1987).
McKiernan and Hull, "The Constituents of Neonatal Milk," Pediatr. Res. 16:60-64 (1982).
Melegh, et al., "Changes of Plasma Free Amino Acids and Renal Clearances of Carnitines in Premature Infants During L-Carnitine-Supplemented Human Milk Feeding", (1998) J. Pediatric Gastroenterol. Nutr. 7(3):424-429.
Moro et al., "Fortification of Human Milk: Evaluation of a Novel Fortification Scheme and of a New Fortifier," J. Ped. Gastroenterol. Nutr. 20:162-172 (1995).
Moro, G.E., et al., "Growth and Metabolic Responses in Low-Birth-Weight Infants Fed Human Milk Fortified with Human Milk Protein or with a Bovine Milk Protein Preparation," J. Pediatric Gastroenterol. and Nutr. 1991. vol. 13, pp. 150-154.
Ogundele, "Techniques for the storage of human breast milk: implications for anti-microbial functions and safety of stored milk," Eur. J. Pediatr. 159:793-797 (2000).
Panzer et al , "Immune thrombocytopenia in severe hemophilia A treated with high-dose intravenous immunoglobulin," Transfusion 26:69-72 (1986).
PCT/US2006/036827 International Search Report and Written Opinion, 5 pages, mailed on Mar. 20, 2008.
PCT/US2007/019234 International Search Report and Written Opinion, 4 pages, mailed on Jan. 24, 2012.
PCT/US2007/085969 International Search Report and Written Opinion, 6 pages, mailed on May 29, 2009.
PCT/US2007/086973 International Search Report and Written Opinion, 6 pages, mailed on Jun. 8, 2009.
Polberger, S.K.T., "Fortified Human Milk for Very Low Birth Weight Infants: Effects on Growth and Metabolism," Dept. Pediatrics, University of Lund, Malmo 1990, pp. 1-148.
Polberger, S.K.T., et al., "Amino Acid Concentrations in Plasma and Urine in Very Low Birth Weight Infants Fed Non-Protein-Enriched or Human Milk Protein-Enriched Human Milk," Department of Pediatrics, University of Lund, Malmö General Hospital, S-21401 Malmö Sweden, pp. 131-148. Pediatrics 1990; 86: 909-915.
Polberger, S.K.T., et al., "Assessment of Eleven Different Plasma Proteins as Indicators of Protein Nutritional Status in Very Low Birth Weight Infants," Department of Pediatrics, University of Lund, Malmö General Hospital, S-21401 Malmö Sweden, 1990, pp. 115-129.
Polberger, S.K.T., et al., "Concentrations of Twelve Plasma Proteins at Birth in Very Low Birth Weight and in Term Infants," Department of Pediatrics, University of Lund, Malmö General Hospital, S-21401 Malmö Sweden, pp. 101-114. Acta Paediatr Scand. 1990; 79(8-9): 729-736.
Polberger, S.K.T., et al., "Growth of Very Low Birth Weight Infants on Varying Amounts of Human Milk Protein," Department of Pediatrics, University of Lund, Malmö General Hospital, S-21401 Malmö Sweden, pp. 69-87. Pediatr Res 1989; 25: 414-419.
Polberger, S.K.T., et al., "Urinary and Serum Urea as Indicators of Protein Metabolism in Very Low Birth Weight Infants Fed Varying Human Milk Protein Intakes," Department of Pediatrics, University of Lund, Malmö General Hospital, S-21401 Malmö Sweden, pp. 89-99. Acta Paediatr Scand. 1990; 79(8-9): 737-42.
Prentice, A., "Constituents of Human Milk," *Food and Nutrition Bulletin*, the United Nations University Press, 17(4), Dec. 1996.
Roennholm, K.A.R., et al., "Human Milk Protein and Medium-Chain Triglyceride Oil Supplementation of Human Milk: Plasma Amino Acids in Very Low-Birth-Weight-Infants," Pediatrics, American Academy of Pediatrics, 74(5):792-799, Jan. 1, 1984.
Ronnholm, K., et al., "Supplementation with Human Milk Protein Improves Growth of Small Premature Infants Fed Human Milk," Pediatrics. 1986. vol. 77, No. 5, pp. 649-653.
Saiki et al., "Genetic analysis of amplified DNA with immobilized sequence-specific oligonucleotide probes," Proc. Natl. Acad. Sci. USA 86:6230-6234 (1989).
Salle, et al., "Effects of Calcium and Phosphorus Supplementation on Calcium Retention and Fat Absorption in Preterm Infants Fed Pooled Human Milk", (1986) J. Pediatric Gastroenterol. Nutr. 5(4):638-642.
Schanler et al., "Feeding strategies for premature infants: beneficial outcomes of feeding fortified human milk versus preterm formula," Pediatr. 103(6 Pt 1):1150-1157 (1999).
Schanler, R., et al., "Enhanced Fecal Excretion of Seleted Immune Factors in Very Low Birth Weight Infants Fed Fortified Human Milk," Pediatric Research. 1986. vol. 20, No. 8, pp. 711-715.
Schanler, R., et al., "Fortified Mothers' Milk for Very Low Birth Weight Infants; Results of Growth and Nutrient Balance Studies," J. Pediatrics. 1985. vol. 107, No. 3, pp. 437-444.
Schanler, R., et al., "Fortified Mothers' Milk for Very Low Birth Weight Infants: Results in Macromineral Balance Studies," J. Pediatrics. 1985. vol. 107, No. 5, pp. 767-774.
Schanler, R., et al., "Mineral Balance Studies in Very Low Birth Weight Infants Fed Human Milk," J. Pediatrics. 1988. vol. 113, vol. 1, Part 2, pp. 230-238.
Srinivasan, L., et al., "Increased Osmolality of Breast Milk with Therapeutic Additives," Arch Dis Child Fetal Neonatal Ed. 2004. 89:F514-17.
Supplementary European Searcg Report maied Oct. 15, 2010, in co-pending related European application No. EP 07 86 5463, 6 pages.
Supplementary European Search Report mailed Apr. 20, 2011 in co-pending European application No. EP 07811645.6, 7 pages.
Supplementary European Search Report mailed Apr. 27, 2011 in co-pending European application No. EP 07864921.7, 8 pages.
Supplementary European Search Report mailed Mar. 24, 2009 in co-pending European application No. EP 06815100.0, 6 pages.
Supplementary European Search Report mailed Oct. 29, 2012 in co-pending European application No. EP 09831061.8, 5 pages.
Terpstra, et al., "Antimicrobial and Antiviral Effect of High-Temperature Short-Time (HTST) Pasteurization Applied to Human Milk," Breastfeeding Med. 2007. vol. 2, pp. 27-33.
The Dairy Council, "The Nutritional Composition of Dairy Products," pp. 1-49, 2002.
Tully, "Is Pasteurized Mother's Own or Donor Milk an Answer to the HIV Crisis," J. Hum. Lact. 15(4):345-346 (1999).

(56) References Cited

OTHER PUBLICATIONS

Virus Safety Services, Sanquin Research, Final Report FR4500, "Process Validation Breast Milk Step 1 for Inactivation of BVDV/HAV/HIV/PSR," May 27, 2002. pp. 1-33.

Voyer, M., et al. "Human Milk Lacto-Engineering," Acta Paediatr Scan. 1984. vol. 73, pp. 302-306.

Williams et al., "Human Milk Banking," J. Trop. Pediatr. 31:185-190 (1985).

Young, "International Search Report," and "Written Opinion of the International Searching Authority," 11 pages, from International Patent Application No. PCT/US09/66430, United States Patent and Trademark Office, Alexandria, Virginia, USA (mailed Jan. 26, 2010).

* cited by examiner

COMPOSITIONS OF HUMAN LIPIDS AND METHODS OF MAKING AND USING SAME

CROSS-REFERENCE TO RELATED APPLICATIONS

This application is a Continuation of U.S. application Ser. No. 12/518,237 filed May 17, 2010, which is a U.S. National Phase entry of PCT Application No. PCT/US2007/086973 which claims priority to provisional application U.S. Ser. No. 60/869,150 filed Dec. 8, 2006. The contents of each of which are incorporated herein by reference in their entirety.

TECHNICAL FIELD

The present disclosure relates to compositions that include lipids from human milk and methods of making and using such compositions.

BACKGROUND

Nutritional support can be administered to the patients in need of it, e.g., enterally or parenterally (e.g., by a process called total parenteral nutrition). Both enteral and parenteral formulas generally include carbohydrates, lipids, proteins, fiber, and/or vitamins and minerals, depending on the needs of a patient. Parenteral formulas may include other additives, such as heparin, H2 blocker etc. The sources of lipids used in parenteral formulas are generally bovine milk, soy, safflower oil, olive oil, and fish oil.

SUMMARY

This disclosure features compositions that include lipids from human milk, methods of obtaining such compositions, and methods of using such compositions to provide nutrition to patients, e.g., human patients.

Nutritional support can be administered to the patients in need of it, e.g., enterally or parenterally (e.g., by a process called total parenteral nutrition). Both enteral and parenteral formulas generally include carbohydrates, lipids, proteins, fiber, and/or vitamins and minerals, depending on the needs of a patient. Parenteral formulas may include other additives, such as heparin, H2 blockers etc. The sources of lipids used in parenteral formulas are generally bovine milk, soy, safflower oil, olive oil, and fish oil. The present disclosure features compositions that include lipids from human milk and that can be used to provide nutritional support to human patients. The compositions can include omega-3 and/or omega-6 fatty acids (and their derivatives and precursors). The compositions may be supplemented, if desired, with, e.g., emulsifiers, preservatives and/or other nutritional constituents. Without being bound by theory, it is believed that use of human lipids may reduce the incidence of liver damage that can occur in patients undergoing TPN that includes non-human lipid sources. Use of human lipids in enteral compositions may also be more beneficial when compared to non-human lipids.

The methods featured herein can be carried out with large volumes of the starting material, e.g., human milk, or pooled human milk. The volumes can be in the range of about 75 liters to about 2,000 liters/lot of the starting material.

In one aspect, the disclosure features a method of making a composition that includes a human lipid. The method includes: (a) obtaining whole human milk; (b) separating the milk into a cream portion and a skim portion; (c) processing the cream portion; and (d) pasteurizing the processed cream portion, thereby obtaining a composition comprising a human lipid.

Embodiments include one or more of the following features.

In one embodiment, the obtaining step includes obtaining from about 75 liters to about 2,000 liters of whole human milk.

In another embodiment, the method further includes: (i) separating the cream portion obtained in step (b) into a second cream portion and a second skim portion; and (ii) in step (c) processing both the cream portion and the second cream portion.

In yet another embodiment, the method also includes filtering water out of the skim portion after step (b). Processing the cream portion includes suspending the cream portion in the water.

In another embodiment, processing the cream portion in step (c) includes precipitating protein components out of the cream portion and/or separating the precipitated protein from the cream portion. Processing the cream portion includes purifying the cream portion, e.g., diafiltrating the cream portion. The processing can further include ultrafiltration. The method further includes, after step (c), adding one or more constituents selected from the group consisting of: an emulsifier, a preservative (e.g., an antioxidant, e.g., alpha-tocopherol, vitamin C, a carotenoid and a retinoid), a diluent, and an osmolality modifier (e.g., glycerin). The method further includes after step (c), adding one or more constituents selected from the group consisting of: a vitamin, a mineral, and a carbohydrate.

In one embodiment, the method further includes administering the composition obtained after step (d) to a subject, e.g., a human subject, e.g., a human infant, e.g., a premature infant. The subject can have a nutritional disease or disorder. The administration is parenteral administration, e.g., part of total parenteral nutritional administration.

In another aspect, the disclosure features a method of making a composition that includes a human lipid. The method includes: (a) obtaining whole human milk; (b) separating the milk into a cream portion and a skim portion; and (c) processing the cream portion, thereby obtaining a composition comprising a human lipid.

Embodiments include one or more of the following features.

In one embodiment, the obtaining step includes obtaining from about 75 liters to about 2,000 liters of whole human milk.

In another embodiment, the method further includes: (i) separating the cream portion obtained in step (b) into a second cream portion and a second skim portion; and (ii) in step (c) processing both the cream portion and the second cream portion.

In yet another embodiment, the method further includes filtering water out of the skim portion after step (b). The processing includes suspending the cream portion in the water.

In another embodiment, the method includes homogenizing the cream portion after step (c). The method includes pasteurizing the cream portion after step (c). The method further includes, after step (c), adding one or more constituents selected from the group consisting of: an emulsifier, a preservative (e.g., an antioxidant, e.g., alpha-tocopherol, vitamin C, a carotenoid, and a retinoid), a diluent, and an osmolality modifier (e.g., glycerin). The method further includes after step (c), adding one or more constituents selected from the group consisting of: a vitamin, a mineral, and a carbohydrate.

In one embodiment, the method further includes administering the composition obtained after step (c) to a subject, e.g., a human subject, e.g., a human infant, e.g., a premature infant. The subject can have a nutritional disease or disorder. The administration is enteral administration.

In another aspect, the disclosure features a composition that includes a human lipid fraction from human milk and an emulsifier.

Embodiments can include one or more of the following features.

In one embodiment, the human lipid fraction includes a pasteurized lipid. The human lipid fraction includes a human polyunsaturated fatty acid, e.g., an omega-3 fatty acid and/or an omega-6 fatty acid. The composition further includes one or more constituents, e.g., an antioxidant (e.g., alpha-tocopherol, vitamin C, a carotenoid and a retinoid), a diluent, an osmolality modifier (e.g., glycerin), a vitamin, a mineral, and/or a carbohydrate.

The disclosure also features a method of treating a subject having a nutritional disease or disorder. The method includes administering to the subject the compositions featured herein (e.g., the composition that includes human lipid fraction from human milk and an emulsifier), thereby treating the subject. The subject is a human subject, e.g., a human infant, e.g., a premature infant.

The terms "premature," "preterm," and "low-birth-weight (LBW)" infants are used interchangeably and refer to infants born less than 37 weeks gestational age and/or with birth weights less than 2500 gm.

By "whole milk" is meant human milk from which no fat has been removed.

As used herein, the term "critically-ill patients" refers to patients who are suffering from a total or partial dysfunction of the gastro-intestinal tract due to prematurity, disease or stress of injury such as surgery, cancer, acute diabetes, AIDS, malnutrition, trauma, ulcerative colitis, necrotizing enterocolitis, or sepsis. The term "critically-ill patients," as used herein, is also intended to include hypercatabolic patients. These critically-ill individuals are often hospitalized and must be administered most or all of their daily nutritional requirements enterally or parenterally in order to sustain protein synthesis and to minimize the likelihood of becoming malnourished, to maintain nutritional status, or to improve nutritional status.

All patents, patent applications, and references cited herein are incorporated in their entireties by reference. Unless defined otherwise, technical and scientific terms used herein have the same meaning as that commonly understood by one of skill in the art.

DETAILED DESCRIPTION

Figure 1:
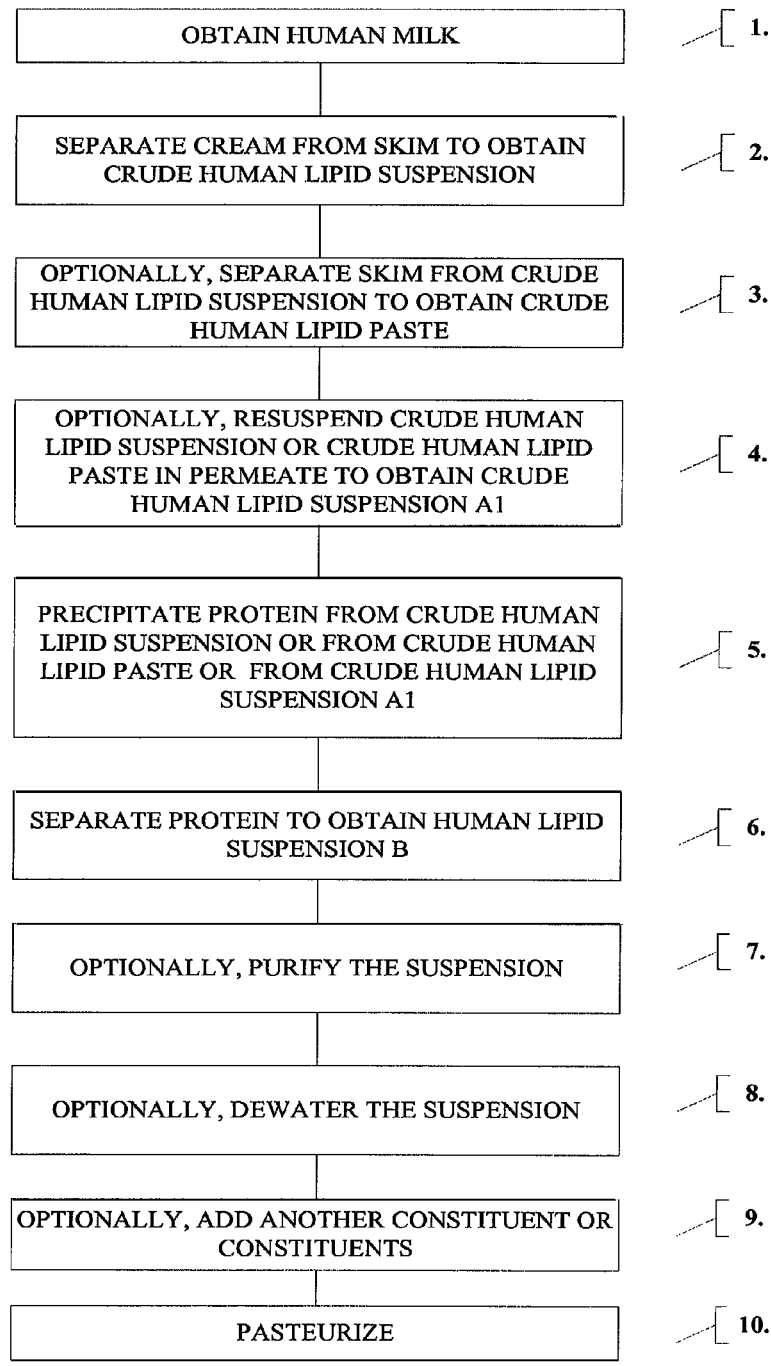
FIG. 1 is a flow chart of an embodiment of making a composition that includes human lipids for TPN.

This disclosure features compositions that include lipids from human milk, methods of obtaining such compositions and methods of using such compositions to provide nutrition to patients, e.g., human patients.

Human subjects, e.g., critically-ill patients, post-operative patients, patients suffering from a nutritional disease or disorder, and/or premature infants, often require administration of nutritional support. Nutritional support can be administered to patients enterally or parenterally (e.g., by a process called total parenteral nutrition or TPN).

Total parenteral nutrition (TPN) is a practice of intravenous feeding, which bypasses eating and digestion. Enteral nutrition is a practice of tube feeding, e.g., nasogastric, transpyloric, and percutaneous. Both enteral and parenteral formulas generally include carbohydrates, lipids, proteins, fiber, and/or vitamins and minerals, depending on the needs of a patient.

As mentioned above, lipids are an important component of both the enteral and the total parenteral nutrition. The present disclosure provides methods of obtaining compositions that include human lipids and that can be used in both enteral and parenteral nutrition, e.g., premature infant enteral and parenteral nutrition. The compositions can include omega-3 and/or omega-6 fatty acids (and their derivatives and precursors). The compositions can be supplemented with other constituents, e.g., emulsifiers, preservatives, diluents, osmolality modifiers, and/or other nutritional components (e.g., vitamins, minerals, and/or carbohydrates). Without being bound by theory, it is believed that use of human lipids may reduce the incidence of liver damage that can occur in patients undergoing TPN that includes non-human lipid sources. Use of human lipids in enteral compositions may also be more beneficial when compared to use of non-human lipids.

The methods featured herein can be carried out with large volumes of the starting material, e.g., human milk, or pooled human milk. The volumes can be in the range of about 75 liters to 2,000 liters/lot of starting material.

Enteral and Parenteral Nutrition

Total parenteral nutrition (TPN) is a practice of intravenous feeding, which bypasses eating and digestion. Enteral nutrition is a practice of tube feeding, e.g., nasogastric, transpyloric, and percutaneous. Each practice has known benefits and drawbacks, and skilled practitioners can choose one mode over the other, depending on individual patient's needs. Both enteral and parenteral formulas generally include carbohydrates, lipids, proteins, fiber, and/or vitamins and minerals, depending on the needs of a patient. Parenteral formulas may include other additives, such as heparin, H2 blocker etc.

Subjects in need of nutritional support include, e.g., premature infants, post-surgical patients, patients with a nutritional disease or disorder, and critically-ill patients. For example, premature infants may have limited capacity of the stomach, deformed organs, and/or immaturity of metabolism. Post-surgical patients may not have the ability to feed themselves. Critically-ill patients may need nutritional support for a variety of reasons. Critically-ill patients can include those with severe burns, trauma, and catabolic states.

One group of patients who need supplemental nutrition includes those with malnutrition. For example, protein calorie malnutrition is a common complicating condition in patients with alcoholic chronic liver disease (Mendenhall et al., *Am. J. Med.* 76:211-222, 1984; Mendenhall et al., *Am. J. Clin. Nutr.* 43:213-218, 1986) and nonalcoholic chronic liver disease (O'Keefe et al. *Lancet* 2:615-617, 1980; Morgan et al. *Gut* 1976; 17:113-118). Patients with end stage liver disease complicated by portal hypertension are particularly likely to be malnourished and, when hospitalized, frequently require active nutritional therapy. While the effects of malnutrition in chronic liver disease on fatty acid nutrition have not been extensively studied, it is believed that because of an increased resting energy expenditure, fat malabsorption and abnormal fat catabolism, these patients may have significant abnormalities in fatty acid metabolism (Cabre et al., *Am. J. Gastroent.* 83:712-717, 1988; Palombo et al., *Gastroent.* 93: 1170-1177, 1987). Without being bound by theory, one potential mechanism for such a disturbance would be an inadequate intake of essential fatty acids as part of the global protein calorie malnutrition.

A patient who is administered a TPN solution containing only saccharides, electrolytes and amino acids for a prolonged period generally will exhibit the symptoms of an essential fatty acid deficiency, such as scale efflorescence, eczematoid eruption, retarded wound healing, thrombocytopenia, fat swelling, anemia and the like. The deficiency is developed within about four to six weeks from the start of TPN, especially when the energy source is only saccharides. Such essential fatty acid deficiency (which is rare in humans who obtain routine nutrition) can be avoided by administering an essential fatty acid-rich fat emulsion concomitantly during TPN therapy.

Lipid emulsions or other preparations containing, e.g., omega-3 fatty acids, are used in TPN and enteral nutritional treatments. For example, they are useful in treating severe trauma victims and subjects with disseminate intravascular coagulation.

Lipids Derived from Human Milk

As noted above, the sources of lipids used in TPN generally include bovine milk, soy, olive oil, and fish oil. This disclosure provides methods of obtaining and using lipids from human milk. The compositions featured herein contain human lipids, which can include both omega-3 and omega-6 fatty acids. Without being bound by theory, it is believed that use of human lipids in TPN may reduce the incidence of liver damage that can occur in patients undergoing TPN that includes non-human lipid sources. Similarly, use of human lipids may be beneficial in enteral nutrition.

Human milk comprises about 100,000 different molecular entities—proteins, lipids, carbohydrates, vitamins, and trace minerals. Human milk contains about 3% to 5% of total lipids that exist as emulsified globules coated with a membrane derived from a secreting cell (Jensen et al., *J. Dairy Sci.* 73:223-240, 1990). The lipids present in human milk include: triacylglycerol (about 98%), phospholipids (about 0.5-1%), and sterols (about 0.2 to 0.5%, e.g., cholesterol) (Jensen et al., supra). Triacylglycerols serve as, e.g., storage molecules of fatty acids.

Different fatty acids in lipids have different physiological, biochemical and, in some cases, pharmacological properties. Dietary fatty acids are classified, e.g., according to their chain length. Long chain fatty acids contain 16 carbons or more and can be further characterized by the number of double bonds contained in their structure (into saturated, monounsaturated and polyunsaturated subgroups). The two fatty acids essential in human nutrition are linoleic acid and alpha-linolenic acid, from which polyunsaturated fatty acids (PUFA) of the omega-6 series and omega-3 series, respectively, are formed. Examples of omega-3 fatty acids include eicosapentaenoic acid (EPA) and docosahexonenoic acid (DHA). Examples of omega-6 fatty acids include gamma linoleic acid (GLA), dihomo-gamma linoleic acid (DGLA), and arachidonic acid (AA). The body cannot convert omega-3 fatty acids to omega-6 fatty acids or vice versa.

Lipids in human milk represent the main source of energy for the breastfed baby and provide essential nutrients, such as fat-soluble vitamins and PUFA. Long chain polyunsaturated fatty acids (LC-PUFA) are key structural components of cellular membranes and are deposited in the growing brain and the retina during perinatal development. Addition of preformed LC-PUFA to human milk lipids has been shown to be related to improved visual acuity and development of cognitive functions during the first year of life in the recipient infants.

Human milk content of fatty acids can vary, depending on the diet of the mother. For example, docosahexaenoic acid (DHA) is a 20 carbon omega-3 fatty acid. If the mother often eats fish high in DHA, her milk will generally contain higher DHA levels than the milk of a mother with less access to fish. Consequently, human milk may require DHA supplementation to insure sufficient amounts of DHA. DHA supplementation is typically accompanied by arachidonic acid supplementation. For example, U.S. Pat. No. 5,492,938, describes a method of obtaining DHA from dinoflagellates and its use in pharmaceutical composition and dietary supplements.

The methods described herein include generating compositions with specific amounts of desired beneficial omega-3 and omega-6 fatty acids.

Human Milk Donors

The starting material of the methods featured herein is human milk. Human milk is collected from donors by systematic methods, described, e.g., in U.S. application Ser. No. 11/947,580 filed Nov. 29, 2007, and in U.S. patent application Ser. No. 11/526,127 (U.S. 2007/0098863). The contents of both applications are incorporated herein by reference in their entireties. The methods featured herein can be carried out with large volumes of human milk, e.g., pooled human milk. The volumes can be in the range of about 75 liters to about 2,000 liters/lot of starting material. Once the milk is collected, it can be frozen, pooled, and processed to obtain a composition of human lipids.

Methods of Obtaining Human Lipid Compositions for TPN

The methods described herein generate human lipid compositions suitable, e.g., for TPN administration. The methods will utilize some components generated in the methods of obtaining human milk fortifiers (HMFs) described in U.S. application Ser. No. 11/947,580 filed on Nov. 29, 2007 (incorporated herein by reference in its entirety), as further explained below.

Referring to FIG. 1, step 1, human milk is obtained from donors, as described above. If frozen, the milk can be thawed, pooled, warmed to about 25° C., and genetically screened for contaminants, e.g., viral contaminants, as described in U.S. Ser. No. 11/947,580. The milk then undergoes filtering, e.g., through about a 200 micron filter, and heat treatment (at about 63° C. or greater for about 30 minutes or more). The milk is transferred to a separator, e.g., a centrifuge, to separate the cream from the skim (step 2). This process intermediate is referred to as Crude Human Lipid Suspension A. The skim can be transferred into a second processing tank, e.g., until a filtration step.

In an optional step 3, the cream component can be separated once more (e.g., by centrifugation) to remove additional skim. This process intermediate is referred to as Crude Human Lipid Paste.

In an optional step 4, the Crude Human Lipid Paste can be re-suspended in excess permeate from the HMF manufacturing process of U.S. Ser. No. 11/947,580. This process intermediate is referred to as Crude Human Lipid Suspension A1. In the HMF process, following separation of cream and skim the skim undergoes further filtration, e.g., ultrafiltration. Ultrafiltration is a type of membrane filtration, in which hydrostatic pressure forces a liquid against a semipermeable membrane; solids and high-molecular weight solutes are retained, while water and low-molecular weight solutes pass through the membrane. Here, this process concentrates the nutrients in the skim milk by filtering out the water. The water obtained during the concentration is referred to as the permeate. This permeate can be used in optional step 4 of the present methods.

In step 5, any remaining protein components not bound to lipids can be precipitated from solution by manipulating various parameters (e.g., temperature, ionic strength, and solvent (e.g., ethanol or polyethylene glycol (PEG) concentration). Such precipitation techniques are known by those skilled in the art. The precipitated proteins can be used in various nutritional supplements.

In step 6, precipitated proteins can be separated from the lipid suspension (e.g., by centrifugation). This process intermediate is referred to as Human Lipid Suspension B.

In an optional step 7, soluble and insoluble salts, other ions, and small molecular entities can be removed from the lipid suspension via a purification process (e.g., diafiltration). Diafiltration is a process, in which ultrafiltration membranes are used to remove or lower the concentration of salts or solvents, or to replace buffer salts from solutions that contain large molecules, such as lipids. This process intermediate is referred to as Diafiltrate A. In optional step 8, the diafiltrate can be dewatered (e.g., by ultrafiltration). This process intermediate is referred to as Purified Human Lipid Suspension.

In an optional step 9, additional constituent(s) can be added to the resulting composition. The constituents can include: an emulsifier, a preservative, a diluent, an osmolality modifier, and a nutritional component (e.g., mineral, vitamin, and carbohydrate). Examples of such constituents are discussed below.

In step 10, the Purified Human Lipid Suspension will be pasteurized, yielding a final product. Pasteurization methods are known in the art. For example, the suspension can be pasteurized at a minimum of about 66 degrees Celsius with the air space maintained at about 69 degrees Celsius for a minimum of about thirty minutes. In one embodiment, the pasteurization can be a short-time (less than about 10 minutes) and ultra-high temperature pasteurization.

Specific order and/or combination of these steps can be adjusted, if desired.

Methods of Obtaining Human Lipid Compositions for Enteral Administration

The methods described herein generate human lipid compositions suitable, e.g., for enteral administration. The methods will utilize some components generated in the methods of obtaining human milk fortifiers (HMFs) described in U.S. application Ser. No. 11/947,580 filed on Nov. 29, 2007, as further explained below.

Figure 2:
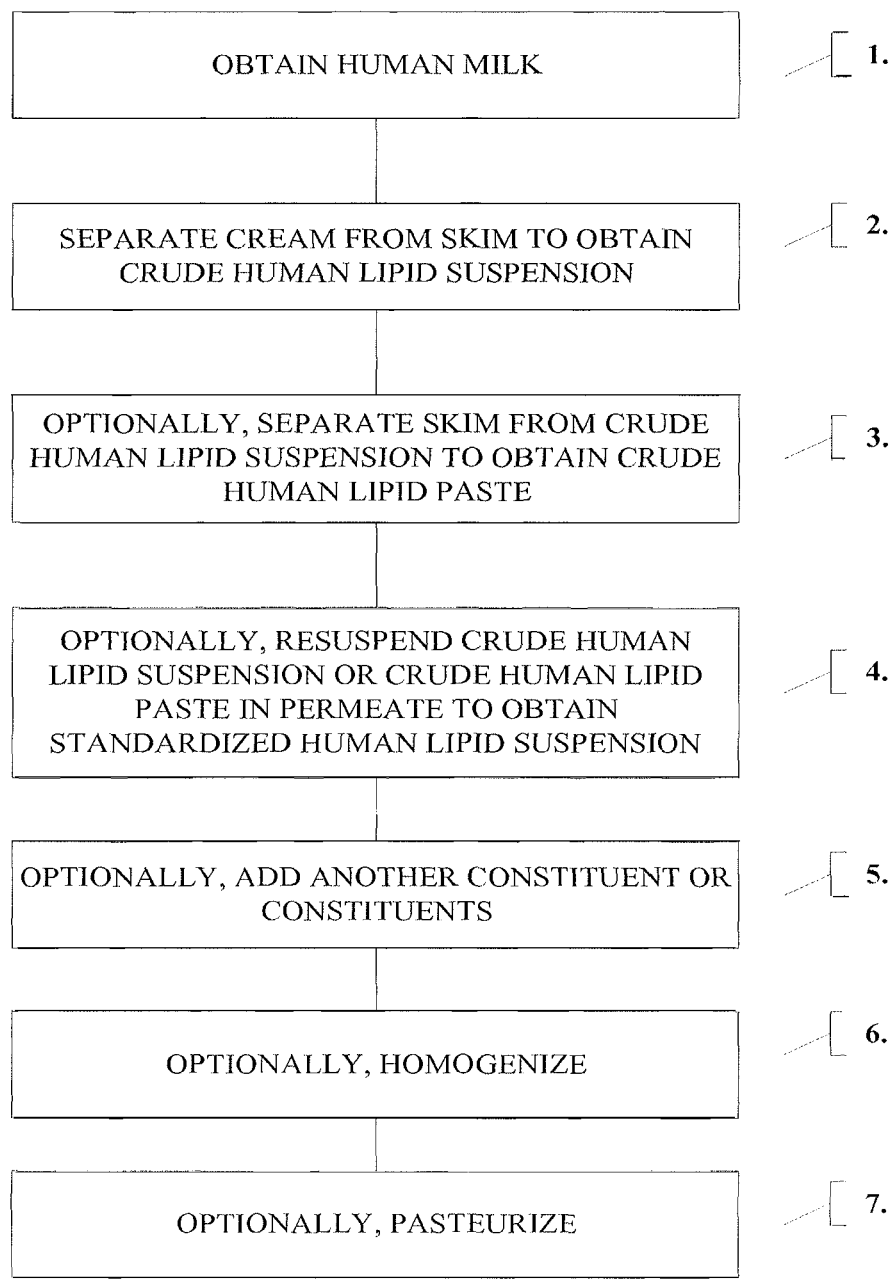
FIG. 2 is a flow chart of an embodiment of making a composition that includes human lipids for enteral administration.

Referring to FIG. 2, step 1, human milk is obtained from donors, as described above. If frozen, the milk can be thawed, pooled, warmed to about 25° C., and genetically screened for contaminants, e.g., viral contaminants, as described in U.S. Ser. No. 11/947,580. The milk then undergoes filtering, e.g., through about a 200 micron filter, and heat treatment (e.g., at about 63° C. or greater for about 30 minutes or more). The milk is transferred to a separator, e.g., a centrifuge, to separate the cream from the skim (step 2). This process intermediate is referred to as Crude Human Lipid Suspension. The skim can be transferred into a second processing tank, e.g., until a filtration step.

In an optional step 3, the cream component can be separated once more (e.g., by centrifugation) to remove additional skim. This process intermediate is referred to as Crude Human Lipid Paste.

In an optional step 4, either the Crude Human Lipid Suspension or the Crude Human Lipid Paste can be re-suspended in excess permeate from the HMF manufacturing process (of U.S. Ser. No. 11/947,580) to achieve a specific lipid density. This process intermediate is referred to as Standardized Human Lipid Suspension. In the HMF process, following separation of cream and skim the skim undergoes further filtration, e.g., ultrafiltration. This process concentrates the nutrients in the skim milk by filtering out the water. The water obtained during the concentration is referred to as the permeate. This permeate can be used in optional step 4 of the present methods.

In an optional step 5 additional constituent(s) can be added to the resulting composition. The constituents can include: an emulsifier, a preservative, a diluent, an osmolality modifier, and a nutritional component (e.g., mineral, vitamin, and carbohydrate). Examples of such constituents are discussed below.

In an optional step 6, the Standardized Human Lipid Suspension is homogenized, using any method familiar to one skilled in the art. Homogenization removes phospholipids from the membranes. The homogenization step can be carried out earlier than step 6 of the process.

In an optional step 7, the Standardized Human Lipid Suspension (homogenized or non-homogenized) can be pasteurized prior to filling into a suitable container (e.g., a bottle or an oral syringe). Pasteurization methods are known in the art, for example the Suspension can be pasteurized, e.g., at a minimum of about 66 degrees Celsius with the air space maintained at about 69 degrees Celsius for a minimum of about thirty minutes. In one embodiment, the pasteurization can be a short-time (less than about 10 minutes) and ultra-high temperature pasteurization.

Specific order and/or combination of the steps outlined above can be adjusted, if desired.

Human Lipid Compositions for TPN and Enteral Administration

The present disclosure features compositions of human lipids useful, e.g., in TPN and enteral administration. The compositions can be obtained by the methods discussed herein.

In one embodiment, the composition includes a human lipid fraction. The lipid fraction can be pasteurized and/or can include polyunsaturated fatty acids, e.g., omega-3 and omega-6 fatty acids (or their derivatives or precursors). The composition can be administered parenterally or enterally. The lipid fraction of the administered composition can provide a source of energy to the subject.

In another embodiment, the composition can include a human lipid and an emulsifier. Emulsifiers can include, e.g., egg yolk phospholipids, hydrogenated egg yolk phospholipids, soybean phospholipids, hydrogenated soybean phospholipids or nonionic surfactants. Emulsifiers can also be, e.g., a purified egg yolk lecithin, a purified soybean lecithin and hydrogenated derivatives thereof, nonionic surfactants, such as Polysorbate 80 and HCO-60. One or more of emulsifiers can also be used in combination in the present enteral and parenteral compositions.

In one embodiment, the compositions described herein can include: about 1-20% (w/v of total emulsion composition) of an emulsifier; about 0.5-50% (w/v) of oil, e.g., 5-30(w/v); about 0.1-80% (w/v) of phospholipids, e.g., 0.1-20% (w/v); and about 0.5-5% of omega-3 fatty acids or derivatives thereof.

The compositions can also include an osmolality modifier, e.g., a polyhydric alcohol, for regulating viscosity of the compositions. The polyhydric alcohols can include, e.g., glycerol and a polyhydric sugar alcohol (e.g., xylitol, sorbitol, and mannitol). Other osmolality modifiers can include glycerin, alanine, sterile water and other modifiers known in the art. One or more osmolality modifiers can also be used in combination in the present compositions.

Optionally, enteral and parenteral compositions described herein can include other constituents, e.g., monoglycerides of fatty acids, diluents (e.g., sugars, starches, lactose, sucrose), preservatives (e.g., antioxidants and anti-microbials), components for adjusting stability (e.g., amino acids), carbohydrates (e.g., fructose and glucose), vitamins, and minerals.

Antioxidants can be added to the compositions to, e.g., protect the unsaturated omega-3 and omega-6 fatty acids (and their precursors and derivatives) from oxidation. Such antioxidants can include alpha-tocopherol (Vitamin E), Vitamin C, carotenoids or retinoids. Other antioxidants that protect the unsaturated omega-3 fatty acids from oxidation after administration and incorporation into biological membranes can also be used.

The emulsion compositions featured herein can be prepared by ways known in the art. For example, the lipids can be mixed with the aqueous phase, the phospholipids (and optionally other emulsifiers), and auxiliary agents in a suitable mixing device. The blend is then homogenized to a desired particle size.

The compositions can also contain stabilizers, such as A-carrageenan. A-carrageenan increases the viscosity of a formula without forming a gel structure, thus retarding the precipitation of insoluble calcium and phosphorus salts if included in the formula. Xanthan gum or other standard stabilizers may also be used.

Flavoring may also be added to the emulsion to make it more palatable for enteral use. Flavoring can be in a form of flavored extracts, volatile oils, chocolate flavoring, peanut butter flavoring, cookie crumbs, vanilla or any commercially available flavoring.

Use of the Compositions

The compositions featured herein can be administered to subjects, e.g., human subjects, in need of nutritional supplementation, e.g., critically-ill patients, post-operative patients, patients suffering from a nutritional disease or disorder, and/or premature infants.

The embodiments of the disclosure may be carried out in other ways than those set forth herein without departing from the spirit and scope of the disclosure. The embodiments are, therefore, to be considered in all respects as illustrative and not restrictive.

Example 1

Obtaining Human Lipid Composition for TPN

The following method will be used to obtain a human lipid composition for TPN administration. This method will utilize some components generated in the methods of obtaining human milk fortifiers (HMFs) described in U.S. application Ser. No. 11/947,580 filed on Nov. 29, 2007, as further explained below.

1. Whole milk will be thawed (if frozen), pooled, and genetically screened for any contaminants, e.g., viral contaminants, as described in U.S. application Ser. No. 11/947,580.

2. Whole milk will be warmed to approximately 25° C. and separated in to skim milk and cream components (e.g., by centrifugation). For example, the separation will occur as described for HMF manufacturing in U.S. Ser. No. 11/947,580. The whole milk will be warmed to 25° C., filtered (e.g., through about a 200 micron filter), heat-treated at about 63° C. or greater for about 30 minutes, and transferred to a separator, e.g., a centrifuge. After separation in to cream and skim, the cream process intermediate is referred to as Crude Human Lipid Suspension A.

3. Optionally, the cream component will be separated once more (e.g., by centrifugation) to remove additional skim. This process intermediate is referred to as Crude Human Lipid Paste.

4. Optionally, the Human Lipid Paste will be re-suspended in excess permeate from the HMF manufacturing process of U.S. Ser. No. 11/947,580. In the HMF manufacturing process, the skim portion separated from the cream undergoes further concentration, e.g., ultrafiltration, to filter out water. The filtered out water is referred to as permeate. This permeate can be used in the method described herein. This process intermediate is referred to as Crude Human Lipid Suspension A1.

5. Any remaining protein components not bound to lipid will be precipitated from solution by manipulating various parameters (e.g., temperature, ionic strength, and solvent (e.g., ethanol or PEG concentration)). These techniques are known to those skilled in the art.

6. Precipitated proteins will be separated from the lipid suspension (e.g., by centrifugation). This process intermediate is referred to as Human Lipid Suspension B.

7. Optionally, soluble and insoluble salts, other ions, and small molecular entities will be removed from the lipid suspension via a purification process (e.g., diafiltration). This process intermediate is referred to as Diafiltrate A.

8. The diafiltrate will be dewatered (e.g., by ultrafiltration). This process intermediate is referred to as Purified Human Lipid Suspension. If desired, emulsifiers and/or preservatives will be added.

9. The Purified Human Lipid Suspension will be pasteurized, yielding a final product.

Example 2

Obtaining Human Lipid Composition for Enteral Nutrition

The following method will be used to obtain a human lipid composition for enteral administration. This method will utilize some components generated in the methods of obtaining human milk fortifiers (HMFs) described in U.S. application Ser. No. 11/947,580 filed on Nov. 29, 2007, as further explained below.

1. Whole milk will be thawed (if frozen), pooled, and genetically screened for any contaminants, e.g., viral contaminants, as described in U.S. application Ser. No. 11/947,580.

2. Whole milk will be warmed to approximately 25° C. and separated in to skim milk and cream components (e.g., by centrifugation). For example, the separation will occur as described for HMF manufacturing in U.S. Ser. No. 11/947,580. The whole milk will be warmed to 25° C., filtered (e.g., through about a 200 micron filter), heat-treated at about 63° C. or greater for about 30 minutes, and transferred to a separator, e.g., a centrifuge. After separation in to cream and skim, the cream process intermediate is referred to as Crude Human Lipid Suspension.

3. Optionally, the cream component may be separated once more (e.g. by centrifugation) to remove additional skim. This process intermediate is referred to as Crude Human Lipid Paste.

4. Optionally, either the Crude Human Lipid Suspension or the Crude Human Lipid Paste will be re-suspended in excess permeate from the HMF manufacturing process (of U.S. Ser.

No. 11/947,580) to achieve specific lipid density. In the HMF manufacturing process, the skim portion separated from the cream undergoes further concentration, e.g., ultrafiltration, to filter out water. The filtered out water is referred to as permeate. This permeate can be used in the method described herein. This process intermediate is referred to as Standardized Human Lipid Suspension.

5. Optionally, the Standardized Human Lipid Suspension will be homogenized.

6. Optionally, the standardized suspension will be pasteurized prior to filling into a suitable container (e.g., a bottle or an oral syringe).

Other variations and embodiments of the invention described herein will now be apparent to those of ordinary skill in the art without departing from the scope of the invention or the spirit of the claims below.

What is claimed is:

1. A method of making a composition comprising a human lipid, the method comprising:
   (a) obtaining whole human milk;
   (b) separating the milk into a cream portion and a skim portion;
   (c) purifying the cream portion obtained in step (b) to obtain a composition comprising a human lipid;
   (d) pasteurizing the composition comprising a human lipid; and
   (e) parenterally administering the composition comprising a human lipid obtained in step (c) to a human subject.

2. The method of claim 1 wherein the purifying comprises diafiltration.

3. The method of claim 1 further comprising adding one or more constituents to the composition obtained in step (d) selected from the group consisting of an emulsifier, a preservative, a diluents, and an osmolality modifier.

4. The method of claim 3, wherein the preservative is an antioxidant.

5. The method of claim 4, wherein the antioxidant is selected from the group consisting of alpha-tocopherol, vitamin C, a carotenoid, and a retinoid.

6. The method of claim 3, wherein the osmolality modifier comprises glycerin.

7. The method of claim 1 further comprising adding one or more constituents to the compostion obtained in step (d) selected from the group consisting of a vitamin, a mineral and a carbohydrate.

8. The method of claim 1 wherein the subject has a nutritional disease or disorder.

9. The method of claim 1 wherein the subject is a premature infant.

* * * * *